US010920174B2

(12) United States Patent
Argo et al.

(10) Patent No.: US 10,920,174 B2
(45) Date of Patent: Feb. 16, 2021

(54) SANITIZING SOAP PREPARATIONS COMPRISING AN AMPHOTERIC/CATIONIC SURFACTANT MIXTURE

(71) Applicant: GPCP IP Holdings LLC, Atlanta, GA (US)

(72) Inventors: Brian Patrick Argo, Greenville, WI (US); Varsha Shah, Greenville, WI (US); Molly Ryan Callahan, Appleton, WI (US)

(73) Assignee: GPCP IP Holdings LLC, Atlanta, GA (US)

( * ) Notice: Subject to any disclaimer, the term of this patent is extended or adjusted under 35 U.S.C. 154(b) by 0 days.

(21) Appl. No.: 16/430,333

(22) Filed: Jun. 3, 2019

(65) Prior Publication Data
US 2019/0352578 A1 Nov. 21, 2019

Related U.S. Application Data

(63) Continuation of application No. 15/659,076, filed on Jul. 25, 2017, now Pat. No. 10,308,897.

(60) Provisional application No. 62/489,222, filed on Apr. 24, 2017.

(51) Int. Cl.
*C11D 1/90* (2006.01)
*C11D 1/62* (2006.01)
*C11D 1/835* (2006.01)
*C11D 3/33* (2006.01)
*A61Q 19/10* (2006.01)
*C11D 1/94* (2006.01)
*C11D 3/48* (2006.01)
*A61K 8/41* (2006.01)
*A61K 8/44* (2006.01)
*A61Q 17/00* (2006.01)
*C11D 1/88* (2006.01)

(52) U.S. Cl.
CPC .............. *C11D 1/62* (2013.01); *A61K 8/416* (2013.01); *A61K 8/44* (2013.01); *A61K 8/442* (2013.01); *A61Q 17/005* (2013.01); *A61Q 19/10* (2013.01); *C11D 1/835* (2013.01); *C11D 1/94* (2013.01); *C11D 3/33* (2013.01); *C11D 3/48* (2013.01); *C11D 1/88* (2013.01)

(58) Field of Classification Search
CPC .... C11D 1/62; C11D 1/75; C11D 1/90; C11D 3/0094; C11D 3/48
See application file for complete search history.

(56) References Cited

U.S. PATENT DOCUMENTS

| | | | |
|---|---|---|---|
| 4,192,894 A | 3/1980 | Botre | |
| 5,547,990 A | 8/1996 | Hall | |
| 5,705,532 A * | 1/1998 | Modak | A01N 47/44 514/635 |
| 5,980,925 A | 11/1999 | Jampani | |
| 5,994,383 A | 11/1999 | Dyer | |
| 6,087,400 A | 6/2000 | Dyer | |
| 6,365,200 B1 | 4/2002 | Birnholz | |
| 6,607,716 B1 * | 8/2003 | Smith | A61K 8/042 424/642 |
| 7,112,559 B1 | 9/2006 | Mayhall | |
| 7,271,137 B2 | 9/2007 | Tucker | |
| 7,858,569 B2 | 12/2010 | Glick | |
| 8,003,594 B2 | 8/2011 | Cunningham | |
| 8,193,136 B2 | 6/2012 | Taylor | |
| 8,333,954 B2 | 12/2012 | Seidling | |
| 8,598,106 B2 | 12/2013 | Schwarz | |
| 9,095,134 B2 | 8/2015 | Eder | |
| 9,204,633 B2 | 12/2015 | Weaver | |
| 9,314,017 B2 | 4/2016 | Myntti | |
| 9,427,417 B2 | 8/2016 | Myntti | |
| 9,486,420 B1 | 11/2016 | Myntti | |
| 9,693,564 B2 | 7/2017 | Reubens | |
| 2001/0044393 A1 | 11/2001 | Peterson | |
| 2002/0031486 A1 | 3/2002 | Lunsmann | |
| 2002/0137631 A1 | 9/2002 | Falder | |
| 2002/0142017 A1 | 10/2002 | Simonnet | |
| 2002/0151446 A1 | 10/2002 | Piterski | |
| 2003/0008791 A1 | 1/2003 | Chiang | |
| 2003/0069148 A1 | 4/2003 | Booker | |
| 2004/0047829 A1 | 3/2004 | Hahn | |
| 2004/0102354 A1 | 5/2004 | Fack | |
| 2005/0049169 A1 * | 3/2005 | Mizushima | A61K 8/42 510/424 |
| 2005/0175568 A1 | 8/2005 | Asari | |
| 2005/0232894 A1 | 10/2005 | Weiner | |
| 2006/0171971 A1 | 8/2006 | Marsh | |
| 2006/0292086 A1 * | 12/2006 | Curtis | A61K 8/046 424/47 |

(Continued)

FOREIGN PATENT DOCUMENTS

| | | |
|---|---|---|
| EP | 655236 | 10/1998 |
| EP | 1032263 | 6/2004 |

(Continued)

OTHER PUBLICATIONS

Versene Chelating Agents, Metal Ion Control for Hard Surface Cleaners, Dow Chemical Co., Oct. 2001.
Crumbliss, Alvin L., "Iron Chelation in Biology", Virtual Free Radical School, http://www.medicine.uiowa.edu/FRRB/VirtualSchool/Crumbliss-Fe.pdf. published online, 2002.

*Primary Examiner* — Charles I Boyer

(57) ABSTRACT

Anti-microbial compositions for cleaning and sanitizing skin are disclosed. The anti-microbial compositions preferably comprises at least one quaternary ammonium chloride active and results in low irritation cleansing and sanitizing products that allow more frequent application.

19 Claims, No Drawings

(56) References Cited

U.S. PATENT DOCUMENTS

| | | |
|---|---|---|
| 2006/0293197 A1 | 12/2006 | Uehara |
| 2007/0031365 A1* | 2/2007 | Terada ............... A61K 8/891 |
| | | 424/70.122 |
| 2007/0149435 A1 | 6/2007 | Koenig |
| 2007/0248691 A1 | 10/2007 | Glick |
| 2007/0253991 A1 | 11/2007 | Glick |
| 2008/0095861 A1 | 4/2008 | Walker |
| 2008/0254150 A1 | 10/2008 | Rheins |
| 2008/0275113 A1 | 11/2008 | Huetter |
| 2009/0246163 A1 | 10/2009 | Wahi |
| 2009/0318322 A1 | 12/2009 | Taylor |
| 2009/0324737 A1 | 12/2009 | Walker |
| 2010/0003341 A1 | 1/2010 | Besendorfer |
| 2011/0070316 A1* | 3/2011 | Modak ............... A01N 33/12 |
| | | 424/642 |
| 2011/0123645 A1* | 5/2011 | Burt ................. A61K 8/35 |
| | | 424/719 |
| 2011/0207886 A1 | 8/2011 | Wakabayashi |
| 2011/0262558 A1* | 10/2011 | Huckfeldt ........... A61K 8/19 |
| | | 424/618 |
| 2012/0021025 A1 | 1/2012 | Bendejacq |
| 2012/0022037 A1* | 1/2012 | Terada ............... A61K 8/39 |
| | | 514/188 |
| 2013/0108679 A1 | 5/2013 | Butterfield |
| 2014/0024688 A1 | 1/2014 | Callahan |
| 2014/0086857 A1 | 3/2014 | Blizzard |
| 2014/0199249 A1 | 7/2014 | Cooper |
| 2014/0378550 A1 | 12/2014 | Grundhofer |
| 2015/0073051 A1 | 3/2015 | Cohen |
| 2015/0290100 A1 | 10/2015 | Eder |
| 2016/0075971 A1 | 3/2016 | Liu |
| 2016/0354302 A1 | 12/2016 | Mitchell |
| 2016/0374352 A1 | 12/2016 | Modak |
| 2017/0015945 A1 | 1/2017 | Larson |
| 2018/0085324 A1* | 3/2018 | Redmond ........... A61K 31/045 |

FOREIGN PATENT DOCUMENTS

| | | |
|---|---|---|
| EP | 1713437 | 4/2008 |
| EP | 2957600 | 12/2015 |
| WO | 2007038855 | 4/2007 |
| WO | 2009050447 | 4/2009 |
| WO | 2012051727 | 4/2012 |
| WO | 2015181558 | 12/2015 |
| WO | 2016019627 | 2/2016 |

* cited by examiner

SANITIZING SOAP PREPARATIONS COMPRISING AN AMPHOTERIC/CATIONIC SURFACTANT MIXTURE

This disclosure relates to an anti-microbial or sanitizing composition for cleaning and sanitizing skin. Additionally, the disclosure relates to rinse-free and rinse-off compositions that comprise at least one quaternary ammonium chloride composition that provides anti-microbial activity. This disclosure further relates to soap compositions and methods of using those compositions to provide low irritation cleansing and sanitizing to skin to allow more frequent cleansing. According to one embodiment, low-irritation quaternary ammonium chloride sanitizing compositions can be produced by improving the efficacy of quaternary ammonium chloride actives to thereby allow a reduction in the concentration of actives needed. According to one embodiment, the improved sanitizing effect can be achieved in quaternary ammonium chloride compositions by reducing the level of the non-active organic compounds present in the sanitizing composition. According to another embodiment, the improved sanitizing effect can be achieved by using specific combinations of different chain lengths in quaternary ammonium chloride compositions to provide synergies that improve anti-microbial effect. According to yet another embodiment, the improved sanitizing effect can be achieved by stabilizing the quaternary ammonium chloride composition at an alkaline pH.

BACKGROUND

Medical professionals have long touted that frequent hand washing reduces the spread of viruses and bacteria. Sanitizing compositions and anti-microbial soaps have become ever present in most public establishments in recent years. Hospitals, schools, office buildings, and private homes are all using anti-microbial rinse-off or rinse-free products to keep everyone safer from bacterial and viral infections. Sanitizing compositions, for example, rinse-free gel hand sanitizers, generally use high alcohol contents to attain their anti-microbial activity. Rinse-free compositions are not formulated to remove soil and therefore, many establishments use both rinse-free formulations, as well as, rinse-off formulations to address both cleaning and sanitizing. Rinse-off cleansers use a variety of anti-microbial agents that, when combined with the mechanical action of washing, significantly reduce bacteria and viruses found on the skin.

Current commercial rinse-off sanitizers can including one or more anti-microbials, anti-bacterials, germicides, etc. and generally use active ingredients chosen from one or more of iodine compounds, peroxide and per-oxygen compositions, alcohols, phenolics, quaternary ammonium compounds, or chlorine compounds. Studies on the efficacy of such sanitizing compositions against specific viruses and bacteria abound. No single composition shows activity as against all of the most common bacteria and viruses. Recently, one of the most prevalent anti-microbials, Triclosan®, has found disfavor and is being removed from consumer products based on a lack of proven efficacy above that of basic soap and water. So, there continues to be a search for sanitizing compositions that are non-hazardous, environmentally friendly, highly effective, and non-irritating.

Both commercial sanitizing compositions and anti-microbial soaps suffer from similar skin irritation problems. In environments such as hospitals, schools, and the food service industry, handwashing/sanitizing is frequent and can be very irritating to the skin of the user. Generally, when anti-microbial products irritate the skin, the user applies the product less frequently. Failure to apply the product as often as needed, increases the likelihood of microbial contamination. The high levels of anti-microbial actives needed to attain commercially suitable activity are a primary cause of the irritation experienced upon frequent use, so there continues to be much research into new actives or ways to reduce the level of actives by making them more effective. Ideally, a cleansing product or sanitizing product would exhibit the necessary anti-microbial activity while remaining gentle and non-drying to the skin, with little or no irritation.

The present disclosure describes anti-microbial soaps and sanitizers that are non-hazardous, environmentally friendly, and substantially less irritating than most current commercial products.

SUMMARY

The present disclosure describes a sanitizing cleansing composition comprising at least one quaternary ammonium chloride surfactant, for example, benzalkonium chloride surfactant, comprising a mixture of compounds having carbon chain lengths of from $C_6$ to $C_{20}$ and wherein the composition comprises at least 80% $C_{12}$ and $C_{14}$ compounds and at least about 0.1% to about 5% $C_6$ to $C_{10}$ compounds.

The present disclosure further describes an anti-microbial cleansing composition comprising at least one quaternary ammonium chloride surfactant, at least one non-quaternary amphoteric surfactant, ethylenediaminetetraacetic acid, and having a pH that is at least 10.0.

The present disclosure describes an anti-microbial cleansing composition comprising at least one quaternary ammonium chloride surfactant, where the non-active organic content of the cleansing composition is below about 8% based on the total weight of the composition.

A better understanding of the various disclosed system and method embodiments can be obtained when the following detailed description is considered in conjunction with the drawings.

DETAILED DESCRIPTION

The following discussion is directed to various embodiments of the invention. Although one or more of these embodiments may be preferred, the embodiments disclosed should not be interpreted, or otherwise used, as limiting the scope of the disclosure, including the claims. It is to be fully recognized that the different teachings of the embodiments discussed below may be employed separately or in any suitable combination to produce desired results. In addition, one skilled in the art will understand that the following description has broad application, and the discussion of any embodiment is meant only to be exemplary of that embodiment, and not intended to intimate that the scope of the disclosure, including the claims, is limited to that embodiment.

Certain terms are used throughout the following description and claims to refer to particular features or components. As one skilled in the art will appreciate different persons may refer to the same feature or component by different names. This document does not intend to distinguish between components or features that differ in name but not structure or function.

In the following discussion and in the claims, the terms "including," "comprising," and "is," are used in an openended fashion, and thus should be interpreted to mean "including, but not limited to."

"Sanitize," as used herein, is meant to include complete elimination of pathogens, as well as any clinically or quantitatively measurable killing, neutralizing, reducing, eliminating, or inhibiting the growth of the pathogen, including bacteria, germs, viruses, molds, or other susceptible pathogens.

"Biocidal," "biocide," and "anti-microbial" as used herein, are meant to include a compound or composition exhibiting any clinically or quantitatively measurable killing, neutralizing, reducing, eliminating, or inhibiting the growth of a pathogen, including bacteria, germs, viruses, molds, or other susceptible pathogens.

"Sanitizing compositions" as described herein are compositions that sanitize a surface upon application of the composition to that surface. Sanitizing compositions can include products for application to hard surfaces, as well as products for application to living tissue, e.g., skin surfaces.

"Non-active organic content" as used herein, refers to the organic compounds that are included in the composition that do not contribute to the biocidal activity of the composition, and include additives such as fragrances, colorants, and the like.

The sanitizing compositions as described herein are water-based systems that contain biocidal agents chosen from quaternary ammonium compounds, herein referred to as "quats," to produce effective, and non-irritating hand soap or hand sanitizer compositions. Quats have been widely used in antimicrobial and disinfectant products for decades and remain popular because they have strong biocidal activity, they are stable over a large pH range, they have low toxicity, and they are cost effective. The biocidal agents can be combined with one or more of a surfactant system, a potentiator, a stabilizer, a solubilizer, a moisturizer, a humectant, a fragrance, or any other class of compounds that are compatible with the biocidal actives and are typical for use in biocidal products.

According to one embodiment, the sanitizing composition as described herein comprises at least one quaternary ammonium compound or composition to disinfect and sanitize the hands of a user, by applying the formulation in a foam and then rubbing the hands together and rinsing with water, referred to herein as a "rinse-off" composition. According to another embodiment, the sanitizing composition as described herein comprises at least one quaternary ammonium compound or composition to disinfect and sanitize the hands of a user, by applying the formulation in a liquid or non-foam form, also as a rinse-off composition.

According to another embodiment, the sanitizing composition as described comprises at least one quaternary ammonium compound or composition to disinfect and sanitize the hands without the need to rinse the composition off with water, referred to herein as a "rinse-free" composition.

Biocidal agents that can be incorporated into the sanitizing composition include one or more quaternary ammonium compounds, of the formula:

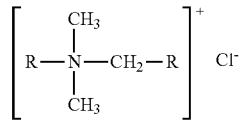

where R can be chosen from a saturated or unsaturated, substituted or unsubstituted, cyclic or straight chain hydrocarbon residue having from 6 to 20 carbon atoms. Examples of quats for use in the present disclosure include, benzalkonium chlorides (BZKs), alkyl dimethyl benzyl ammonium chlorides (ADBAC); benzethonium chlorides also known by (diisobutylphenoxyethoxyethyl)-dimethylbenzylammonium chlorides methylbenzethonium chlorides, dioctyl ammonium chloride and didecyl dimethyl ammonium chloride (DDAC). While the present description uses the benzalkonium chloride as exemplary, the skilled artisan would recognize that the statements, and examples throughout, apply equally when using a different quaternary compound, for example, benzethonium chloride.

According to one embodiment, the sanitizing composition may comprise a benzalkonium chloride composition as the biocidal agent. According to this embodiment, the active agent can be a quaternary ammonium composition wherein R has differing carbon chain lengths.

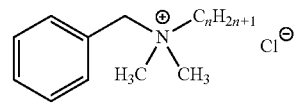

n = 6, 8, 10, 12, 14, 16, 18, 20

According to one embodiment, the biocidal agent can be a composition of n-alkyl dimethyl benzyl ammonium chloride. According to this embodiment, the composition can include benzalkonium chlorides wherein R has chain lengths between 6 and 20 carbon atoms. The benzalkonium composition may be chosen from any art recognized benzalkonium compositions that have anti-microbial or biocidal properties.

Benzalkonium chloride compositions for use in the present disclosure may be specially manufactured or may be produced from combinations of commercially available benzalkonium chloride compositions. Benzalkonium chlorides are routinely sold as compositions defined by the weight percent of the composition that has a particular chain length. So, a commercial benzalkonium composition may be characterized, for example, as having 20 to 80% $C_{12}$ compounds, 20 to 80% $C_{14}$ compounds, and 0 to 40% $C_{16}$ compounds. Commercially available compositions may be combined for use in the sanitizing products as described. The instant disclosure discusses benzalkonium chloride actives with reference to their overall composition in the sanitizing product regardless of whether they are from a single source or multiple sources and whether they are combined together before being added to the sanitizing composition, or not.

According to one embodiment, the biocidal agent can include STEPANQUAT 50 produced by Stepan Company, wherein R comprises about 50% $C_{12}$ compounds, about 30% $C_{14}$ compounds, about 17% $C_{16}$ compounds and about 3% $C_{18}$ compounds. According to another embodiment, the biocidal agent may include a benzalkonium composition chosen from STEPANQUAT 65, produced by Stepan Company, in which R comprises about 67% $C_{12}$ compounds, about 25% $C_{14}$ compounds, about 7% $C_{16}$ compounds and about 1% $C_8$, $C_{10}$, $C_{18}$ compounds. According to another embodiment, the sanitizing composition may include benzalkonium compositions chosen from STEPANQUAT 8358, in which R comprises about 40% $C_{12}$ compounds, about 50% $C_{14}$ compounds, about 10% $C_{16}$ compounds. Other benzylalkonium chlorides that may be used in the described biocidal compositions may be purchased from Sigma Aldrich under the tradenames Benxalkonium chloride, Benzalkonium chloride BioXtra or Benzalkonium chloride PharmaGrade; from Akzo Nobel under the Arquad name; from Pilot under the name Maquat; and from Solvay Chemical according to CAS number.

In addition to discovering that the anti-microbial active is more effective when the sanitizing composition has an alkaline pH of greater than 10, and that the anti-microbial active is more effective when the non-active organic content of the sanitizing composition is limited, it has also been discovered that benzalkonium chloride compositions having specific combinations of side chain lengths can also provide a greater efficacy/irritation profile, in each instance making it possible to reduce the amount of active material without sacrificing performance to create a less irritating product.

More particularly, benzalkonium chloride compositions having carbon side chain lengths of from $C_6$ to $C_{20}$, where the compositions comprise at least 80% $C_{12}$ and $C_{14}$ side chain compounds and at least about 0.1% to about 5% $C_6$ to $C_{10}$ compounds are described. The benzalkonium chloride compositions according to this embodiment can, of course, be used in the described formulations that have alkaline pH or limited non-active organic content, as described. Not wishing to be bound by theory, it is believed that $C_6$, $C_8$ and $C_{10}$ BZK compounds may behave as hydrotropes or solvents, and their inclusion improves the mass transfer of the higher chain length benzalkonium chlorides such as $C_{12}$ and $C_{14}$. Because the shorter chain quats behave more as a solvent than a surfactant, they change the nature of the bulk solvent system enabling the higher chain length quats to move through the bulk solution more rapidly thereby improving the biocidal efficacy and reducing the killing time for microbes. $C_{12}$ or $C_{14}$ BZK compounds are those having the greatest activity, while $C_{16}$ or $C_{18}$ BZK compounds are more likely to be substantive to skin. Sanitizing compositions as described benefit from the described distribution of chain lengths and the inclusion of $C_6$ to $C_{10}$ compounds.

According to this embodiment, the benzalkonium chloride composition may be chosen from one or more of the embodiments in Table 1, below.

TABLE 1

Benzalkonium Chloride Carbon Chain Length Distribution

| $C_6$ | $C_8$ | $C_{10}$ | $C_{12}$ | $C_{14}$ | $C_{16}$ | $C_{18}$ | $C_{20}$ |
|---|---|---|---|---|---|---|---|
| 0 to 3% | 0 to 15% | 0.0 to 19% | 0 to 80% | 0 to 80% | 0 to 10% | 0 to 10% | 0 to 3% |
| 0 to 3% | 0.5 to 1.5% | 0.5 to 1.5% | 45 to 70% | 10 to 55% | 0 to 12% | 0 to 2.0% | 0 to 3% |
| 0.1% to 3% | 0 to 15% | 0 to 19% | 0 to 80% | 0 to 80% | 0 to 15% | 0 to 15% | 0 to 15% |
| | 2% to 3% | | | 80% to 99% | 0 to 18% | 0 to 18% | 0 to 18% |
| | 0.1% to 3% | | | 90% to 99% | 0 to 18% | 0 to 18% | 0 to 18% |
| | 0.1% to 3% | | | 80% to 99% | 0 to 5% | 0 to 5% | 0 to 5% |
| 0.1% to 3% | | 0% | | 75% to 99% | 0 to 15% | 0 to 15% | 0 to 15% |
| 0% | 0.5% | 0.5% | 58.5% | 27.5% | 12.0% | 2.0% | 0% |

The quaternary ammonium chloride active agent(s) may be present in the sanitizing composition in an amount of from about 0.05% to about 0.75%, for example, from about 0.1% to about 0.6%, for example, from about 0.1% to about 0.3%. All percentages used herein are weight percentages and refer to the biocidal agent based upon the overall sanitizing composition.

Other active agents that are compatible with the biocidal agents described above may be included in the sanitizing composition. Other compatible active agents include, but are not limited to non-ionic surfactants, hydrotropes, chelating agents, preservatives, alcohols, e.g., ethanol, and biocidally active botanical extracts, for example, essential oils, and like. These compatible active agents may be present in an amount of from about 0.01% to about 7.0%, for example, from about 0.5% to about 5.0%, for example, from about 1.5% to about 3.0%.

As defined herein, the non-active organic content can include, dyes, moisturizing agents, skin conditioning agents, thickeners, solvents, vitamins, anti-oxidants, pH modifiers, film formers, anti-inflammatories, abrasives, colorants, humectants, emollients, fragrances, and botanical extracts, excluding biocidally active essential oil, for example, pine oil, thyme oil, and/or peppermint oil.

The pH of the system is maintained from about 5 to about 13. Depending upon the embodiment, the pH may be alkaline, e.g., above about 10, or may be more neutral, from about 5 to about 9, for example, in low organic systems. The system pH will be discussed in more detail with respect to individual embodiments.

The sanitizing compositions as described herein may comprise one or more surfactants chosen from amphoteric surfactants, anionic surfactants, cationic surfactants or non-ionic surfactants.

Amphoteric surfactants for use in the sanitizing composition as described include, but are not limited to, dodecyl/dimethyl amine oxide marketed under the tradename AMMONYX LO from Stepan Co. and cocamidopropyl betaine marketed under the tradename AMPHOSOL HCP-HP both from Stepan Co. Appropriate amphoteric surfactants are readily available and are marketed by companies such as Akzo Nobel, Pilot and Solvay Chemical. Amphoteric surfactant will be present in the sanitizing composition in an amount of from about 0.01% to about 3.0%, for example, from about 0.5% to about 2.5%, for example, from about 0.75% to about 2.0%.

Anionic surfactants are defined as those surfactants that possess a negative charge and include such surfactant classes as sulfates, sulfonates, sulfosuccinates, taurates, isethionates, alkanoic acids, ester carboxylic acids and ether carboxylic acids. Nonionic surfactants are defined as those surfactants possessing no charge moieties within the molecular structure and include such surfactant classes as alkanol amines, alkanolamides, ethoxylated amides, ethoxylated fatty acids, ethoxylated fatty alcohols, alkoxylated esters, alkyl polyglucosides, alkoxylated triglycerides, sorbitan esters and sorbitan ethers.

Cationic surfactants are defined as those surfactants that possess a positive charge and include such surfactant classes as benzalkonium, stearalkonium, and centrimonium chlorides, trimethyl ammoniums, and methyl sulfates.

The anionic, cationic and non-ionic surfactants can be present in the sanitizing composition in an amount of from about 0% to about 5.0%, for example, from about 0.5% to about 4.0%, for example, from about 1.5% to about 3.0%.

The sanitizing composition as described herein can comprise one or more compounds that act as potentiators to improve the efficacy of the biocidal activity of the active agents. Materials that can be incorporated into the Palisade Layer of micelles can often increase the mass transfer kinetics of materials such as BZK when applied at concentrations at or below 0.1%. Such potentiators can be chosen from one or more terpenes, such as tetrahyromyrcenol, cis-2-pinanol, pinanol, thymol, 1,8-terpin, dihydro-terpineol, tetrahydrolinalool, tetrahydro-alloocimenol, and terpen ethers including benzyl isoamyl ether, 1,8-cineole, 1,4-cineole, isobornyl methyl ether, methyl hexylether; polyols and diols. The potentiator will be present in the sanitizing composition in an amount of from about 0% to about 0.4%, for example, from about 0% to about 0.2%, for example, from about 0% to about 0.1%.

Optional ingredients that may be added to the formulation include, for example, emollients, fragrances, dyes, humectants, moisturizing agents, skin conditioning agents, chelating agents, preservatives, thickeners, solvents, botanicals, vitamins, anti-oxidants, pH modifiers, film formers, anti-inflammatories, abrasives, colorants, and the like.

Depending upon the embodiment, optional stabilizers may be used to inhibit reactions between ingredients and to maintain the homogeneity of the composition. According to one embodiment, if the sanitizing composition is a foaming composition, it may include one or more foam stabilizers. Suitable foam stabilizers can be chosen from foam boosters, alkyl polyglucosides, amphoteric surfactants, nonionic surfactants, amide oxides. The stabilizer will be present in the sanitizing composition in an amount of from about 0% to about 10%, for example from about 0.01% to about 5%, for example, from about 0.01% to about 2%.

Appropriate solubilizers for use in the sanitizing compositions as described will be readily apparent to the skilled artisan and can include hydrotropes, nonionic, surfactants, chelating agents, builders. The solubilizer can be present in the sanitizing composition in an amount of from about 0% to about 5%, for example, from about 0% to about 2.0%, for example, from about 0.1% to about 2.0%.

Generally, emollients lubricate, soothe, and soften the skin surface. Exemplary emollients include silicons, ethoxylated or propoxylated oily or waxy ingredients such as esters, ethers, fatty alcohols, hydrocarbons, lanolin, and the like. The emollients can be present in the sanitizing composition in an amount of from about 0% to about 10%, for example, from about 0.1% to about 3%, for example, from about 0.05% to about 1%.

Humectants are hydroscopic agents that are widely used as moisturizers. Their function is to prevent the loss of moisture from the skin and to attract moisture from the environment. Common humectants include, for example, sodium PCA, glycerin, propylene glycol, butylene glycol, betaine, sodium hyaluronate, sorbitol, urea, hydroxyethyl urea, and the like. The humectants can be present in the sanitizing composition in an amount of from about 0% to about 5.0%, for example, from about 0.1% to about 2.5%, for example, from about 0.5% to about 1.5%.

Preservatives for increasing the shelf life of the sanitizing composition may also be used. Exemplary suitable preservatives include, but are not limited to disodium EDTA; tetrasodium EDTA; iodopropynyl butylcarbamate; benzoic esters (parabens), such as methylparaben, propylparaben, butylparaben, ethylparaben, sodium methylparaben, and sodium propylparaben; phenoxyethanol; benzyl alcohol; phenethyl alcohol; amidazolidinyl urea; diazolidinyl urea; citric acid, lactic acid, kathon, phenoxyethanol, 2-bromo-2 nitro-propane-1,3,-diol, potassium sorbate, and the like. The preservatives can be present in the sanitizing composition in an amount of from about 0.1 to about 3%, for example, from about 0.1% to about 1%, for example, from about 0.1% to about 0.5%.

Suitable skin conditioning agents include, for example, hydrolyzed plant proteins such as hydrolyzed wheat protein, hydrolyzed soy protein, hydrolyzed collagen, and the like. The skin conditioning agents can be present in the sanitizing composition in an amount of from about 0% to about 10%, for example, from about 0.1% to about 5%, for example, from about 0.5% to about 3%.

pH modifiers include both basic and acidic pH modifiers. Some examples of basic pH modifiers that may be used in the sanitizing compositions of the present disclosure include, but are not limited to, ammonia; sodium, potassium, and lithium hydroxide; sodium, potassium, and lithium metal silicates; monoethanolamine; triethylamine; isopropanolamine; ethanolamine; and triethanolamine. Acidic pH modifiers that may be used in the formulations of the present disclosure include, but are not limited to, mineral acids; carboxylic acids; and polymeric acids, including by way of example, citric acid. The pH modifiers will be used in an amount necessary to achieve the desired pH. For example, the pH modifiers can be present in the sanitizing composition in an amount of from about 0% to about 5%, for example, from about 0.05% to about 3%, for example, from about 0.1% to about 2%. According to one embodiment, the sanitizing composition has a pH in the alkaline range. According to another embodiment, the sanitizing composition has a pH in the neutral/acidic range.

A chelating agent is a substance whose molecules can form one or more bonds with a metal ion. In particular, water that may be contained in the sanitizing composition often contains metal ions, such as calcium ions, that might react with anionic components (e.g., acids) present within the composition. Some examples of chelating agents that may be used in the sanitizing composition of the present disclosure include, but are not limited to, ethylenediamines, ethylenediaminetetraacetic acids (EDTA) acids and/or salts thereof, for example, tetrasodium EDTA, citrate, pyrithione, N,N'-bis(o-hydroxybenzyl)ethylenediamine-N,N'diacetic acid; ethylenebis-N,N'-(2-o-hydroxyphenyl)glycine, 1,3-diaminopropane-N,N,N',N'-tetraacetic acid; ethylenediamine-N,N'-diacetic acid; ethylenediamine-N,N'-dipropionic acid dihydrochloride; ethylenediamine-N,N'-bis(methylenephosphonic acid); N-(2-hydroxyethyl)ethylenediamine-N,N',N'-triacetic acid; ethylenediamine-N,N,N',N'-tetrakis(methylenephosponic acid); O,O'-bis(2-aminoethyl)ethyleneglycol-N,N,N',N'-tetraacetic acid; N,N-bis(2-hydroxybenzyl)ethylenediamine-N,N-diacetic acid; 1,6-hexamethylenediamine-N,N,N',N'-tetraacetic acid; N-(2-hydroxyethyl)iminodiacetic acid; iminodiacetic acid; 1,2-diaminopropane-N,N,N',N'-tetraacetic acid; nitrilotriacetic acid; nitrilotripropionic acid; nitrilotris(methylenephosphonic acid); and triethylenetetramine-N,N,N',N'',N''',N'''-hexaacetic acid, glucuronic acids and/or salts thereof, succinic acid and/or salts thereof, polyphosphates, organophosphates, and the like. Additionally, chelating agents can potentiate the antimicrobial efficacy of benzalkonium chlorides at lower pH, so the addition of the chelating agent may require reducing the concentration of the benzalkonium chloride active ingredient. This reduction in active concentration can reduce cost, as well as improving skin safety. The chelating agent can be present in the sanitizing composition in an amount of from about 0% to about 5%, for example, from about 0.01% to about 3%, for example, from about 0.5% to about 2%. The level of chelating agent, as described, is based upon the chelating agent being EDTA. Other chelating agents should be used at these weight percentages in equimolar quantities to EDTA.

Fragrances and dyes may be used in the sanitizing compositions as appropriate to appeal to the purchasing consumer. Fragrances and dyes can be present in the sanitizing composition in an amount of from about 0% to about 5%, for example, from about 0.1% to about 1%, for example, from about 0.2% to about 0.5%. According to one embodiment, fragrances, dyes and other organic compositions are minimized to obtain the best results using a benzylalkonium active agent.

Moisturizing agents for use in the sanitizing compositions as described can include, but are not limited to collagen; lecithins; liposomes; peptides; polysaccharides; glycerin; sorbitol; propylene glycol; calcium pantothenate; urea; caprylyl glycol; butylene glycol; glucose; magnesium lactate; potassium chloride; potassium lactate; ethylhexylglycerin; dipropylene glycol; silicones, such as dimethicone and cyclomethicone; fatty acids, for example, lanolin acid; fatty alcohols, for example, lanolin alcohol; hydrocarbon oils and waxes; petrolatum; polyhydric alcohols; sterols, for example, cholesterol; vegetable and animal fats, for example, cocoa butter, vegetable waxes, carnauba wax, wax esters, and bees wax; hyaluronic acid, ceramics; caprylic/capric triglycerides; magnesium aspartame; potassium aspartame; sarcosine; and the like. The moisturizing agent can be present in the sanitizing composition in an amount of from about 0% to about 10%, for example, from about 0.1% to about 5%, for example, from about 0.5% to about 3%.

Thickeners for use in the sanitizing composition as described include, for example, cetyl alcohol, stearyl alcohol, carnauba wax, and stearic acid, carboxyethyl cellulose, carboxymethyl cellulose, guar gum, xanthan gum, gelatin, silica, bentonite, silicates, carbomer polymers, and the like. Thickeners can be present in the sanitizing composition in an amount of from about 0% to about 5%, for example, from about 0.1% to about 3%, for example, from about 0.2% to about 1%.

Botanicals for use in the sanitizing compositions as described may include, for example, aloe vera, green tea extract, cucumber extract, chamomile, oat, Aspen Bark, Bamboo Leaf, Banaba Leaf, Burdock Root, Chamomile, Chrysanthemum, Cucumber Peel, Ginkgo Biloba Leaf, Ginseng Root, Grape Seed, Green Tea, Honey Suckle Flower, Horse Chest Nut, Licorice Root, Maca, Milk Thistle (Silymarin), Olive Leaf, Rosehips, Rosemary, Sacha Inchi, Sea Buckthorn, Sunflower, Thyme, White Willow Bark, and the like. Botanicals can be present in the sanitizing composition in an amount of from about 0% to about 5%, for example, from about 0.1% to about 3%, for example, from about 0.1% to about 1%.

Vitamins for use in the sanitizing composition may include for example, Vitamins A, B, C, D, E, tocopheryl acetate, retinyl palmitate, panthenol, and ascorbic acid. Vitamins can be present in the sanitizing composition in an amount of from about 0% to about 5%, for example, from about 0.1% to about 3%, for example, from about 0.1% to about 1%.

Antioxidants for use in the sanitizing composition as described can include one or more of Glutathione, superoxide dismutase, ubiquinone, omega-fatty acids, Vitamin C, Beta-Glucan, Thioctic Acid, Magnesium Ascorbyl, Phosphate, Ferulic Acid, Superoxide Dismutase, Epigallocatechin Gallate, Ergothioneine, Glutathione, Xanthophylls, and the like. Antioxidants may be present in the composition in an amount of from about 0% to about 5%, for example, from about 0.1% to about 3%, for example, from about 0.1% to about 1%.

The artisan skilled in the formulation of soaps or sanitizers understands that ingredients may be selected to provide more than one function in a composition. Thus, a single ingredient may be chosen to act, for example, as a pH modifier and a preservative, or as a moisturizer and as a humectant.

According to one embodiment, the composition as described can be formulated at a pH in the alkaline range, i.e., at a pH of 10 or greater. The increased alkalinity improves the effectiveness of the quaternary ammonium chloride active allowing the concentration of the active(s) to be reduced. According to this embodiment, the active(s) may be reduced on the order of 50%. Increased pH would seem counterintuitive given that the skin has a pH in the acid range and products in the more neutral pH range tend to be less irritating. However, while the pH increase may cause a slight rise in skin irritation, that is more than offset by the reduced irritation that accompanies the use of a lower level of biocidal actives. According to one embodiment, the improvements in efficacy and reductions in irritation can be further improved by the inclusion of EDTA in the sanitizing composition.

According to one embodiment, the alkaline anti-microbial cleaner has a pH of greater than about 11, for example, greater than about 12, for example, greater than about 13. According to another example, the alkaline anti-microbial sanitizer can comprise at least one amphoteric surfactant and at least one preservative. According to another embodiment, the alkaline anti-microbial cleaner can include a benzalkonium chloride active having a least about 0.1% $C_6$-$C_8$ side chains. According to yet another embodiment, the alkaline anti-microbial sanitizer may include less than about 8% non-active organics, for example, less than about 4% non-active organics, for example, less than about 2% non-active organics, for example, less than about 1%, non-active organic actives.

According to one embodiment, a reduction in the level of non-biocidal actives used in the sanitizing composition can improve the efficacy of the quaternary ammonium chloride active. For example, aloe vera is a common ingredient used in sanitizing and biocidal hand preparations because it has excellent emollient properties. However, the inclusion of aloe vera and other skin health modifiers can have a negative impact on the effectiveness of quaternary ammonium chloride active materials. It has been discovered that reducing the amount of organic material in a sanitizing composition having a quaternary ammonium chloride active can provide a substantial improvement in irritation. More specifically, the most irritating part of the sanitizing composition is the active, and when the organics are reduced or eliminated, the amount of the quaternary ammonium chloride active can be reduced to a level that provides sufficient sanitizing activity with little or no irritation. Not wishing to be bound by theory, commercial products have heretofore generally had moisturizers, emollients, and the like to offset some of the harshness of the active agent. It has been discovered that those same organics were interfering with the efficacy of the BZK actives resulting in sanitizers with higher, more irritating levels of active. Once the irritation properties are resolved, the need for humectants, emollients and moisturizers are diminished.

According to one embodiment, compositions having reduced levels of non-active organic compounds may be formulated any art recognized pH, for example, from about 4 to about 9. According to one embodiment, the non-biocidal organics are present in the composition in an amount of less than about 8%, for example, less than about 6%, for example less than about 4%, for example between about 0.5% and 4%, for example, less than about 2%, for example, less than about 1%. According to another embodiment, the low organic content sanitizer can include a benzalkonium chloride active having a least about 0.1% C6-C8 side chains.

According to one embodiment, the cleanser will not only provide sanitizing of the skin with reduced irritation levels, it may also impart moisturizing benefits to the skin. Appropriate to this embodiment, the formulation will include one or more moisturizers, emollients, or humectants. Moisturizing can be added to any of the embodiments as described herein.

As used herein, "about" is meant to account for variations due to experimental error. All numerical measurements are understood to be modified by the word "about", whether or not "about" is explicitly recited, unless specifically stated otherwise. Thus, for example, the statement "an amount of 1 gram," is understood to mean "an amount of about 1 gram."

EXAMPLES

Unless noted otherwise, the benzalkonium chloride actives used in these Examples included a 1:1 blend of Stepanquat 50 and Stepanquat 65. The concentration of actives was 0.13%, 0.26%, or 0.52% total actives. These concentrations of actives result in a carbon chain length distribution within the benzalkonium chloride composition, as follows (0.13%-0.26% being most preferred, and 0.13%-0.56% being preferred):

| Distribution of Carbon Chain Lengths in BZK Raw Materials (%) | | | | | | | |
|---|---|---|---|---|---|---|---|
| Product | $C_6$ | $C_8$ | $C_{10}$ | $C_{12}$ | $C_{14}$ | $C_{16}$ | $C_{18}$ |
| 0.13%-0.56% Products | 0.0 to 0.0 | 0.00065 to 0.00260 | 0.00065 to 0.00260 | 0.08 to 0.30 | 0.04 to 0.14 | 0.02 to 0.06 | 0.003 to 0.010 |
| 0.13% to 0.26% Products | 0.0 to 0.0 | 0.00065 to 0.00130 | 0.00065 to 0.00130 | 0.08 to 0.30 | 0.04 to 0.07 | 0.02 to 0.03 | 0.003 to 0.005 |

Example 1

Benzalkonium cleansing compositions according to the instant disclosure were prepared by combining the ingredients as set forth in Table 2.

TABLE 2

| Trade | INCI name | Ex. 1 Solids Wt % | Ex. 1A Solids Wt % |
|---|---|---|---|
| Deionized Water | Water | 94.099 | 95.599 |
| Amphosol HCP-HP | Cocamidopropyl betaine | 0.99 | 0.99 |
| Ammonyx LO | Lauramine oxide | 1.17 | 1.17 |
| Versene 100 | Tetrasodium EDTA | 0.19 | 0.19 |
| Stepanquat 65 NF | Benzalkonium chloride | 0.125 | 0.125 |
| Stepanquat 50 NF | Benzalkonium chloride | 0.125 | 0.125 |
| Sorbitol | Sorbitol | 1.00 | 0.50 |
| Propylene Glycol | Propylene Glycol | 1.00 | 0.50 |
| Vit E acetate | Vit E acetate | 0.0004 | 0.0004 |
| Extract Cocktail | Extract Cocktail | 0.0004 | 0.0004 |
| Sodium PCA | Sodium PCA | 1.00 | 0.50 |
| Fragrance | Floral Fragrance | 0.20 | 0.00 |
| Fragrance | Floral Fragrance | 0.00 | 0.20 |
| *Aloe* | *Aloe* | 0.10 | 0.10 |
| Green Dye | Dye | 0.0002 | 0.00 |

TABLE 2-continued

| Trade | INCI name | Ex. 1 Solids Wt % | Ex. 1A Solids Wt % |
|---|---|---|---|
| Peach Dye | Dye | 0.00 | 0.0002 |
| Citric Acid | Citric Acid | qs | qs |
| Total | | 100.00 | 100.00 |
| pH | | 10.50 | 10.50 |

The compositions were held and evaluated for stability. At one week, both compositions had significant yellowing and the pH had dropped to 9.9.

Example 2

Samples as described in Example 1, we prepared in the lab at a pH of 10.2 and 10.5, respectively. Under simple observation, the samples at pH 10.2 appeared to have better stability than the samples at pH of 10.5. In order to discover the reason behind this instability, compositions were prepared as in Example 1, with the changes as seen in Table 3.

TABLE 3

| Formula | Initial pH | Total BZK (wt %) | Humectant Level (wt %) | Color | Fragrance |
|---|---|---|---|---|---|
| Sample 1 | 10.20 | 0.25 | 3.0 | — | — |
| Sample 2 | 10.20 | 0.25 | 3.0 | — | Floral |
| Sample 3 | 10.20 | 0.25 | 3.0 | Green Dye | — |
| Sample 4 | 10.20 | 0.25 | 3.0 | Green Dye | Floral |
| Sample 5 | 10.50 | 0.25 | 3.0 | — | — |

TABLE 3-continued

| Formula | Initial pH | Total BZK (wt %) | Humectant Level (wt %) | Color | Fragrance |
|---|---|---|---|---|---|
| Sample 6 | 10.50 | 0.25 | 3.0 | — | Floral |
| Sample 7 | 10.50 | 0.25 | 3.0 | Green Dye | — |
| Sample 8 | 10.50 | 0.25 | 3.0 | Green Dye | Floral |

Cleansing compositions were prepared as described in Example 1, but the levels of dye and fragrance were revised as set forth in Table 3, above. The compositions were adjusted to an initial pH of 10.2. The samples were held under appropriate conditions for four weeks.

As can be seen from Tables 4 and 5, the higher the level of organics the less stable the composition. While not wishing to be bound by theory, it is believed that the reason the largest pH drop occurred in samples with fragrance is because the benzalkonium chloride had a higher solubility in the fragrance systems.

TABLE 4

70° F. pH stability at 0.25% BZK

| Weeks | Dye Free Fragrance Free | FRAGRANCE ALONE | DYE ALONE | BOTH DYE AND FRAGRANCE |
|---|---|---|---|---|
| 0 | 10.20 | 10.20 | 10.20 | 10.20 |
| 1 | 10.00 | 9.76 | 10.01 | 9.73 |
| 2 | 10.05 | 9.74 | 10.04 | 9.73 |
| 4 | 10.01 | 9.70 | 10.00 | 9.69 |

TABLE 5

120° F. pH stability at 0.25% BZK

| Weeks | Dye Free Fragrance Free | FRAGRANCE ALONE | DYE ALONE | BOTH DYE AND FRAGRANCE |
|---|---|---|---|---|
| 0 | 10.20 | 10.20 | 10.20 | 10.20 |
| 1 | 9.95 | 9.68 | 9.96 | 9.68 |
| 2 | 9.90 | 9.58 | 9.87 | 9.68 |

Example 3

Compositions as in Example 2 were prepared, but the initial pH of the formula was adjusted to 10.5. The samples were held under appropriate conditions at 70'F, 100'F or 120'F for up to four weeks. The pHs are set forth below in Tables 6 and 7.

TABLE 6

70° F. pH stability at 0.25% BZK

| Weeks | Dye Free Fragrance Free | FRAGRANCE ALONE | DYE ALONE | BOTH DYE AND FRAGRANCE |
|---|---|---|---|---|
| 0 | 10.50 | 10.50 | 10.50 | 10.50 |
| 1 | 10.31 | 9.95 | 10.30 | 9.95 |
| 2 | 10.34 | 9.95 | 10.64 | 9.80 |
| 4 | 10.28 | 9.91 | 10.28 | 9.78 |

TABLE 7

100° F. pH stability at 0.25% BZK

| Weeks | Dye Free Fragrance Free | FRAGRANCE ALONE | DYE ALONE | BOTH DYE AND FRAGRANCE |
|---|---|---|---|---|
| 0 | 10.50 | 10.50 | 10.50 | 10.50 |
| 1 | 10.28 | 9.84 | 10.33 | 9.92 |
| 2 | 10.21 | 9.85 | 10.2 | 9.86 |
| 4 | 10.14 | 9.85 | 10.17 | 9.86 |

TABLE 8

120° F. pH stability at 0.25% BZK

| Weeks | Dye Free Fragrance Free | FRAGRANCE ALONE | DYE ALONE | BOTH DYE AND FRAGRANCE |
|---|---|---|---|---|
| 0 | 10.50 | 10.50 | 10.50 | 10.50 |
| 1 | 10.15 | 9.84 | 10.13 | 9.87 |
| 2 | 10.03 | 9.72 | 10.02 | 9.78 |

Example 4

The samples of Examples 2 and 3 were also tested for color stability at both one week and one month. The results are set forth in Table 9, below.

TABLE 9

| Formula | Initial pH | Total BZK (wt %) | Humectant Level (wt %) | Color | Fragrance | 70 F. 1 month Color | 100 F. 1 week Color |
|---|---|---|---|---|---|---|---|
| Sample 1 | 10.20 | 0.25 | 3.0 | — | — | Same | Same |
| Sample 2 | 10.20 | 0.25 | 3.0 | — | Floral | Same | Yellow |
| Sample 3 | 10.20 | 0.25 | 3.0 | Green Dye | — | Same | Same |
| Sample 4 | 10.20 | 0.25 | 3.0 | Green Dye | Floral | Same | Yellow |
| Sample 5 | 10.50 | 0.25 | 3.0 | — | — | Same | Same |
| Sample 6 | 10.50 | 0.25 | 3.0 | — | Floral | Same | Yellow |
| Sample 7 | 10.50 | 0.25 | 3.0 | Green Dye | — | Same | Same |
| Sample 8 | 10.50 | 0.25 | 3.0 | Green Dye | Floral | Same | Yellow |

At 70'F, the fragrance color remained stable for 1 month. As can be seen above, un-fragranced formulation maintained good color stability for the entire storage period. Also, crystals formed for the samples when exposed to 120° F., but disappeared upon cooling.

Example 5

Samples were prepared as in Example 1 and were tested against *S. aureus* and *C. albicans* at different pH and humectant levels. The variations and results are set forth in Tables 10-12 below.

TABLE 10

| Formulation | pH = 9.9 |
|---|---|
| 30 second - Log Reduction in *S. areus* | |
| Cyan 3% Humectant | 5.561 |
| Cyan 1.5% Humectant | 6.038 |
| 30 second - Log Reduction in *C. albicans* | |
| Cyan 3% Humectant | 5.327 |
| Cyan 1.5% Humectant | 5.327 |

TABLE 11

30 second - Log Reduction in *S. areus*

| Formulation | pH = 10.2 | pH = 10.5 |
|---|---|---|
| DFFF | 3.907 | 3.084 |
| Fragrance Only | 1.994 | 2.174 |
| Dye Only | 0.000 | 3.017 |
| Dye + Fragrance | 0.000 | 2.177 |

TABLE 12

30 second Log Reduction in *C. albicans*

| Formulation | pH = 10.2 | pH = 10.5 |
|---|---|---|
| DFFF | 1.249 | 1.808 |
| Fragrance Only | 1.117 | 1.586 |
| Dye Only | 1.405 | 2.23 |
| Dye + Fragrance | 1.246 | 1.912 |

As can be seen from Tables 10-12, the products with a lower pH had better antimicrobial efficacy.

Example 6

As series of sample compositions were prepared as in Example 1. The samples vary by amount of benzalkonium chloride, pH and presence of dye or fragrance. The samples were tested for pH stability for up to two weeks. The compositional variations, along with the results, are set forth in Table 13, below. The number value is the initial pH of the sample, followed by the letter D and F. DFFF is dye free, fragrance free. D is dye and F is fragrance.

TABLE 13

| | | | 0.13% 120 F. pH Stability | | | |
|---|---|---|---|---|---|---|
| Weeks | 5.00 DFFF | 7.00 DFFF | 9.00 DFFF | 5.00 D + F | 7.00 D + F | 9.00 D + F |
| 0 | 5.00 | 7.00 | 9.00 | 5.00 | 7.00 | 9.00 |
| 1 | 4.99 | 7.11 | 9.17 | 5.02 | 7.05 | 8.59 |
| | | | 0.26% 120 F. pH Stability | | | |
| Weeks | 9.00 DFFF | 7.00 DFFF | 5.00 DFFF | 9.00 D + F | 7.00 D + F | 5.00 D + F |
| 0 | 5.00 | 7.00 | 9.00 | 5.00 | 7.00 | 9.00 |
| 1 | 4.95 | 7.07 | 9.13 | 4.98 | 7.06 | 8.59 |
| | | | 0.52% 120 F. pH Stability | | | |
| Weeks | 5.00 DFFF | 7.00 DFFF | 9.00 DFFF | 5.00 D + F | 7.00 D + F | 9.00 D + F |
| 0 | 5.00 | 7.00 | 9.00 | 5.00 | 7.00 | 9.00 |
| 1 | 4.98 | 7.12 | 9.11 | 5.05 | 7.06 | 8.53 |

TABLE 14

| Weeks | 5.00 DFFF | 7.00 DFFF | 9.00 DFFF | 5.00 D + F | 7.00 D + F | 9.00 D + F |
|---|---|---|---|---|---|---|
| | | | 100 F. pH Stability 0.13% BZK pH Stability | | | |
| 0 | 5.00 | 7.00 | 9.00 | 5.00 | 7.00 | 9.00 |
| 1 | 5.07 | 7.15 | 9.01 | 5.08 | 7.05 | 8.69 |
| 2 | 5.02 | 7.11 | 9.02 | 5.02 | 7.00 | 8.77 |
| | | | 100 F. pH Stability 0.26% BZK pH Stability | | | |
| 0 | 5.00 | 7.00 | 9.00 | 5.00 | 7.00 | 9.00 |
| 1 | 4.98 | 7.08 | 9.07 | 5.00 | 7.05 | 8.64 |
| 2 | 5.05 | 7.12 | 9.09 | 5.05 | 7.07 | 8.61 |
| | | | 100 F. pH Stability 0.52% BZK pH Stability | | | |
| 0 | 5.00 | 7.00 | 9.00 | 5.00 | 7.00 | 9.00 |
| 1 | 4.98 | 7.08 | 9.07 | 5.00 | 7.05 | 8.64 |
| 2 | 5.04 | 7.12 | 9.13 | 5.13 | 7.1 | 8.62 |

TABLE 15

| Weeks | 5.00 DFFF | 7.00 DFFF | 9.00 DFFF | 5.00 D + F | 7.00 D + F | 9.00 D + F |
|---|---|---|---|---|---|---|
| | | | 70 F. pH Stability 0.13% BZK pH Stability | | | |
| 0 | 5.00 | 7.00 | 9.00 | 5.00 | 7.00 | 9.00 |
| 1 | 5.08 | 7.27 | 8.82 | 5.1 | 7.13 | 8.71 |
| 2 | 5.03 | 7.21 | 8.93 | 5.04 | 7.11 | 8.90 |
| | | | 70 F. pH Stability 0.26% BZK pH Stability | | | |
| 0 | 5.00 | 7.00 | 9.00 | 5.00 | 7.00 | 9.00 |
| 1 | 5 | 7.1 | 9.04 | 5.01 | 7.09 | 8.81 |
| 2 | 4.93 | 7.12 | 9.01 | 5.05 | 6.98 | 8.74 |

TABLE 15-continued

| Weeks | 5.00 DFFF | 7.00 DFFF | 9.00 DFFF | 5.00 D + F | 7.00 D + F | 9.00 D + F |
|---|---|---|---|---|---|---|
| | | 70 F. pH Stability 0.82% BZK pH Stability | | | | |
| 0 | 5.00 | 7.00 | 9.00 | 5.00 | 7.00 | 9.00 |
| 1 | 5.03 | 7.09 | 9.01 | 5.01 | 7.07 | 8.78 |
| 2 | 5.05 | 7.02 | 8.99 | 5.06 | 7.11 | 8.70 |

As can be seen from Tables 13, 14 and 15, the amount of benzalkonium chloride in the sample did not influence the pH stability of the sample.

Example 7

The samples of Example 6 were tested for antimicrobial efficacy as *S. aureus* and *C. albicans*. The results are set forth in Table 16.

TABLE 16

| Formula | 60 sec log Reduction *S. aureus* |
|---|---|
| BZK = 0.26%, pH = 5.0, DFFF | 1.3350 |
| BZK = 0.13%, pH = 9.0, Green D + F | 3.8670 |
| BZK = 0.26%, pH = 7.0, Green D + F | 4.9980 |
| BZK = 0.13%, pH = 7.0, Orange D + F | 2.1500 |
| BZK = 0.13%, pH = 9.0, Orange D + F | 3.4790 |
| BZK = 0.26%, pH = 7.0, Orange D + F | 4.6000 |
| BZK = 0.26%, pH = 9.0, Orange D + F | 5.9980 |

Example 8

The samples of Example 6 were tested for color stability and fragrance stability. Fragrance yellowing only appears in the 120° F. samples, and it was significantly reduced at a pH of 9.0. No other yellowing was observed during the two weeks of stability to date.

The scent of the fragrance did not change over 14 days at 70'F or 100'F. It also appeared to be stable for one week at 120° F.

Example 9

Samples as described in Example 1, were prepared at different pH levels and different organic contents and then were then tested against *S. aureus* and *C. albicans*. The results are set forth in Table 17, below.

TABLE 17

| Formula | pH | BZK | Organic Content (%) | *S. aureus* | 30 Second Exposure-Log Reduction in Microbe *C. albicans* |
|---|---|---|---|---|---|
| Sample A | 10.5 | 0.25 | 1.50 | 6.26 | 5.66 |
| Sample B | 10.5 | 0.25 | 3.00 | 1.36 | 1.92 |
| Sample C | 10.2 | 0.25 | 3.00 | 0.00 | 1.24 |
| Sample D | 7.0 | 0.26 | 0.75 | 3.59 | — |

As the pH drops from 10.5 to 10.2, the antimicrobial efficacy is dramatically reduced. At pH 10.5, when the organic content drops, the antimicrobial efficacy is increased. Even though the pH is reduced to 7.0, because the organic content is also reduced to 0.75%, we see better antimicrobial efficacy than at pH 10.5 with 3% organics. For purposes of this evaluation, the organic content was made up of equal parts sorbitol, propylene glycol, and sodium PCA.

Example 10

Anti-microbial compositions were prepared as in Example 1, but having a pH of 7 and an active level of 0.26% BZK. The efficacy of the composition was measured for 26 different microbes. The test results are set forth in Table 18.

TABLE 18

| Microorganism | Kill Time (15 Seconds) | Kill Time (30 Seconds) | Kill Time (60 Seconds) |
|---|---|---|---|
| *Acinetobacter baumanii* | 5.618 | 5.168 | 5.618 |
| *Bacteroides fragilis* | 4.8603 | 4.8603 | 4.8603 |
| *Candida albicans* | 0.4184 | 0.6568 | 1.1495 |
| *Candida tropicalis* | 1.1205 | 1.6683 | 3.2225 |
| *Enterobacter aerogenes* | 0.1004 | 0.7069 | 3.251 |
| *Enterococcus faecalis* | 5.8195 | 5.8195 | 5.8195 |
| *Enterococcus faecium* | 5.4314 | 5.4314 | 5.0335 |
| *Escherichia coli* (ATCC #1129) | 0.3104 | 2.1273 | 5.2765 |
| *Escherichia coli* (ATCC #25922) | 4.0208 | 5.2292 | 5.2292 |
| *Haemophilus influenzae* | 5.8228 | 5.8228 | 5.8228 |
| *Klebsiella oxytoca* | 0.1684 | 2.1855 | 5.1833 |
| *Klebsiella pneumoniae* | 0.1189 | 1.5574 | 5.3802 |
| *Micrococcus luteus* | 6.5617 | 6.5617 | 6.5617 |
| *Proteus miabilis* | 0 | 0.1688 | 1.8985 |
| *Pseudomona aeruginosa* (AATC #15442) | 2.1198 | 5.4031 | 5.4031 |
| *Pseudomona aeruginosa* (AATC #27853 | 1.9218 | 5.3741 | 5.5502 |
| *Salmonella enterica* serovar *Typhi* (ATCC6359) | 5.301 | 5.301 | 5.301 |
| *Serratia marcescens* | 0 | 0 | 0.1603 |
| *Staphylococcus aureus* (AATC #6538) | 1.1894 | 3.0245 | 5.2613 |
| *Staphylococcus aureus* (AATC #29213) | 0.9471 | 0.6254 | 5.2589 |
| *Staphylococcus epidermidis* | 2.7631 | 4.8325 | 5.7076 |
| *Staphylococcus haemolyticus* | 2.1032 | 4.2543 | 5.0502 |
| *Staphylococcus hominis* | 5.3075 | 5.3075 | 5.3075 |
| *Staphylococcus saprophyticus* | 5.5966 | 5.5966 | 5.5966 |
| *Streptococcus pneumoniae* | 5.2 | 5.2 | 5.2 |
| *Streptococcus pyogenes* | 5.6902 | 5.6902 | 5.6902 |

As can be seen in Table 18, the composition clearly demonstrated efficacy against all microbes that it was tested against.

Example 11—Comparative Example

Compositions as described in Example 1 having an active level of 0.26% BZK and a pH of 7 were compared with a commercially available anti-microbial sanitizer containing triclosan.

TABLE 19

| Microorganism | BZK | Triclosan |
|---|---|---|
| C. Albicans | 0.3 | 0.7 |
| Enterococcus faecalis | 5.0 | 5.0 |
| Escherichia coli (ATCC #25922) | 5.2 | 5.0 |
| Klebsiella pneumoniae | 2.2 | 5.0 |
| Pseudomona aeruginosa | 5.0 | 5.0 |
| Serratia marcescens | 3.0 | 1.2 |

As can be seen in Table 19, the BZK composition provides a kill rate, essentially comparable to Triclosan.

Example 12—Comparative Example

Samples were prepared and subject to the Zein test which assess the relative mildness of the composition. The test performed was based on the Zein Test from the Encyclopedia of Surface and Colloid Science pp. 6142-6146. The sample is combined with zein protein and allowed to react for 60 minutes. The zein slurry is then vacuum filtered and the residue is weighed. The zein loss is the difference between the amount of zein protein before reaction minus the amount of residual zein protein. Results are set forth in Table 20, below.

TABLE 20

| Sample | Zein Loss (%) |
|---|---|
| 2% CHG Foaming Solution (comparison) | 2.8 |
| Deionized Water | 3.6 |
| 0.26% BZK, pH = 7.0 DFFF | 6.0 |
| Steris enMotion High Frequency Soap | 6.2 |
| Pacific Blue Ultra Soap 0.13% BZK | 8.2 |
| Pacific Blue General Purpose Soap | 22.0 |
| Pacific Blue Gentle Foam Soap | 23.0 |
| enMotion DFF, 0.45% Triclosan (Comparison) | 37.6 |

As can be seen from these results, anti-microbial compositions as described herein can achieve up to a 6 fold reduction in zein protein solubility over commercial Triclosan based soaps. As described above, the higher the zein loss the more irritating the product.

Example 12—Rinse Free Composition

Rinse-free sanitizing compositions were prepared by combining the ingredients as set forth in Table 21.

TABLE 21

| Ingredient | Percent of Active Material | Percent of Active Material |
|---|---|---|
| Water | 99.1703 | 99.3803 |
| Decyl Glucoside | 0.1288 | 0.1288 |
| BZK | 0.1000 | 0.1000 |
| Aloe | 0.1000 | 0 |
| Glycerin | 0.1000 | 0.1000 |
| Propylene Glycol | 0.1000 | 0 |
| Panthanol | 0.1000 | 0 |
| PEG-12 Dimethicone | 0.2000 | 0.2000 |
| Dipotassium Phosphate | 0.0500 | 0.0500 |
| Potassium Phosphate | 0.0410 | 0.0410 |

EMBODIMENTS

The following embodiments are exemplary only.

A. An anti-microbial cleansing composition comprising a benzalkonium chloride active composition comprising at least about 0.1% $C_6$ carbon side chains, at least about 80% $C_{12}$-$C_{14}$ side chains and from about 0% to about 18% $C_{16}$-$C_{20}$ side chains; and water.

B. An anti-microbial cleansing composition comprising a benzalkonium chloride active composition comprising at least about 0.1% $C_6$ carbon side chains, at least about 80% $C_{12}$-$C_{14}$ side chains and from about 0% to about 18% $C_{16}$-$C_{20}$ side chains, ethylenediaminetetraacetic acid, and water.

C. An anti-microbial cleansing composition comprising a benzalkonium chloride active composition comprising at least about 0.1% $C_6$ carbon side chains, at least about 85% $C_{22}$-$C_{14}$ side chains and from about 0% to about 18% $C_{16}$-$C_{20}$ side chains; and water.

D. An anti-microbial cleansing composition comprising a benzalkonium chloride active composition comprising at least about 0.1% $C_6$ carbon side chains, at least about 90% $C_{12}$-$C_{14}$ side chains and from about 0% to about 18% $C_{16}$-$C_{20}$ side chains; and water.

E. An anti-microbial cleansing composition comprising a benzalkonium chloride active composition comprising at least about 0.1% $C_6$ to $C_{10}$ carbon side chains, at least about 80% $C_{12}$-$C_{14}$ side chains and less than about 5% $C_{16}$-$C_{18}$ side chains; and water.

F. An anti-microbial cleansing composition comprising a benzalkonium chloride active composition comprising at least about 0.1% $C_6$ to $C_{10}$ carbon side chains, at least about 80% $C_{12}$-$C_{14}$ side chains and less than about 5% $C_{16}$-$C_{18}$ side chains; ethylenediaminetetraacetic acid, and water.

G. An anti-microbial cleansing composition comprising a benzalkonium chloride active composition comprising at least about 0.1% $C_6$ to $C_{10}$ carbon side chains, at least about 85% $C_{12}$-$C_{14}$ side chains and less than about 5% $C_{16}$-$C_{18}$ side chains; and water.

H. An anti-microbial cleansing composition comprising a benzalkonium chloride active composition comprising at least about 0.1% $C_6$ to $C_{10}$ carbon side chains, at least about 90% $C_{12}$-$C_{14}$ side chains and less than about 5% $C_{16}$-$C_{18}$ side chains; and water.

I. An anti-microbial cleansing composition comprising a benzalkonium chloride active composition comprising at least about 0.1% $C_6$ carbon side chains, at least about 80% $C_{12}$-$C_{14}$ side chains and from about 0% to about 18% $C_{16}$-$C_{20}$ side chains; and water.

J. An anti-microbial cleansing composition comprising a benzalkonium chloride active composition comprising at least about 0.1% $C_6$ carbon side chains, at least about 80% $C_{12}$-$C_{14}$ side chains and from about 0% to about 18% $C_{16}$-$C_{20}$ side chains; ethylenediaminetetraacetic acid, and water.

K. An anti-microbial cleansing composition comprising a benzalkonium chloride active composition comprising at least about 0.1% $C_6$ carbon side chains, at least about 85% $C_{12}$-$C_{14}$ side chains and from about 0% to about 18% $C_{16}$-$C_{20}$ side chains; and water.

L. An anti-microbial cleansing composition comprising a benzalkonium chloride active composition comprising at least about 0.1% $C_6$ carbon side chains, at least about 90% $C_{12}$-$C_{14}$ side chains and from about 0% to about 18% $C_{16}$-$C_{20}$ side chains; and water.

Although specific embodiments have been illustrated and described herein, it should be appreciated that any arrangement configured to achieve the same purpose may be substituted for the specific embodiments shown. This disclosure is intended to cover any and all adaptations or variations of various embodiments. Combinations of the above embodiments, and other embodiments not described herein, will be apparent to those of skill in the art upon reviewing the above description.

What is claimed:

1. A skin soap or skin sanitizer anti-microbial cleansing composition comprising:
   A) at least one amphoteric surfactant selected from the group consisting of one or more betaines and amine oxides;
   B) from about 0.1% to about 0.3% of at least one quaternary ammonium chloride surfactant selected from the group consisting of one or more benzalkonium chloride surfactants and benzethonium chloride surfactants, wherein the at least one surfactant comprises an alkyl substituent that is at least 80% $C_{12}$ and $C_{14}$ in carbon chain length;
   C) at least one alkyl trimethyl ammonium cationic surfactant present in an amount of 1.5% to 3.0%;
   D) at least one preservative in the amount of from about 0.1% to about 0.5%;
   E) at least one humectant in an amount of from about 0.1 to about 2.5%; and
   wherein the non-active organic content of the composition is below about 8% of the compositions by weight.

2. The anti-microbial cleansing composition of claim 1, wherein the pH of the composition is from about 5 to about 13.

3. The anti-microbial composition of claim 1, wherein the quaternary ammonium chloride surfactant is one or more benzalkonium chlorides.

4. The anti-microbial composition of claim 3, wherein the benzalkonium chloride comprises an alkyl substituent that is at least 85% $C_{12}$ and $C_{14}$ in carbon chain length.

5. The anti-microbial composition of claim 1, wherein the level of non-active organics is below about 4%.

6. The anti-microbial composition of claim 1, wherein the level of non-active organics is below about 2%.

7. The anti-microbial composition of claim 6, wherein the composition is dye free, fragrance free, or dye and fragrance free.

8. A method of using the skin soap or skin sanitizer anti-microbial cleansing composition of claim 1, comprising;
   applying the cleansing composition to skin of a user; and
   optionally, rinsing the composition from the skin with water.

9. A method of using the skin soap or skin sanitizer anti-microbial cleansing composition of claim 6, comprising;
   applying the cleansing composition to skin of a user; and
   optionally, rinsing the composition from the skin with water.

10. The anti-microbial composition of claim 1, further comprising at least one vitamin in an amount of from about 0.01% to about 5.0%.

11. The anti-microbial composition of claim 10, wherein one of the at least one vitamin is Tocopheryl Acetate.

12. The anti-microbial composition of claim 1, further comprising at least one botanical in an amount of from about 0.01% to about 5.0%.

13. The anti-microbial composition of claim 12, wherein the at least one botanical is chosen from one or more of chamomile extract or oat extract.

14. The anti-microbial composition of claim 1, wherein the at least one amphoteric surfactant is selected from the group consisting of Lauramine Oxide or Cocoamidopropyl Betaine.

15. The anti-microbial composition of claim 1, wherein the at least one amphoteric surfactant is present in an in an amount of from about 0.01% to about 3.0%.

16. The anti-microbial composition of claim 1, wherein the at least one preservative comprises Tetrasodium EDTA.

17. The anti-microbial composition of claim 1, wherein the at least one humectant is selected from the group consisting of Sorbitol, Propylene Glycol, Glycerin or Sodium PCA.

18. The anti-microbial composition of claim 2, wherein the pH of the composition is from about 6 to about 8.

19. A skin soap or skin sanitizer anti-microbial cleansing composition comprising:
   A) at least one betaine in an amount of from about 0.01% to about 3.0%;
   B) from about 0.1% to about 0.3% of at least one quaternary ammonium chloride surfactant selected from the group consisting of one or more benzalkonium chloride surfactants and benzethonium chloride surfactants, wherein the at least one surfactant comprises an alkyl substituent that is at least 80% $C_{12}$ and $C_{14}$ in carbon chain length;
   C) at least one alkyl trimethyl ammonium cationic surfactant present in an amount of 1.5% to 3.0%;
   D) at least one preservative in the amount of from about 0.1% to about 0.5%;
   E) at least one humectant in an amount of from about 0.1 to about 2.5%; and
   wherein the non-active organic content of the composition is below about 8% of the compositions by weight.

* * * * *